United States Patent [19]

Miyazawa et al.

[11] 3,936,564
[45] Feb. 3, 1976

[54] PRESSURE-SENSITIVE COPYING PAPER CONTAINING LACTONE COMPOUNDS OF PYRIDINE-CARBOXYLIC ACID

[75] Inventors: Yoshihide Miyazawa; Minoru Ozutsumi; Satoshi Ogawa, all of Tokyo; Keiso Saeki; Akio Watanabe, both of Fuojimiya, all of Japan

[73] Assignees: Hodogaya Chemical Co., Ltd., Tokyo; Fuji Photo Film Co., Ltd., Minami-ashigara, both of Japan

[22] Filed: July 24, 1974

[21] Appl. No.: 491,193

[30] Foreign Application Priority Data
July 24, 1973   Japan................................ 48-82648

[52] U.S. Cl. ............... 428/307; 282/27.5; 427/145; 427/261; 428/323; 428/325; 428/454
[51] Int. Cl.² ......................................... B41M 5/16
[58] Field of Search ............... 260/295 B; 117/36.1; 282/28 R, 27.5; 428/511, 325, 454, 488, 323, 307; 282/27.5; 427/145, 261

[56] References Cited
UNITED STATES PATENTS
3,775,424   11/1973   Farber............................ 260/295 B
3,853,869   12/1974   Farber............................ 260/250 BC

*Primary Examiner*—Thomas J. Herbert, Jr.
*Attorney, Agent, or Firm*—Sughrue, Rothwell, Mion, Zinn & Macpeak

[57] ABSTRACT

A pressure-sensitive copying paper comprising an adsorbent solid acid and a microencapsulated color former capable of forming a distinct color when reacted with the adsorbent acid coated on the same or a different surface of a support or supports, the microencapsulated color former being at least one lactone compound of a pyridine-carboxylic acid represented by the formula

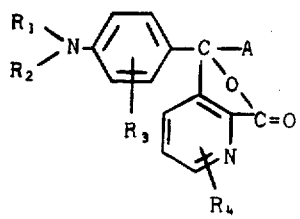

(I)

or

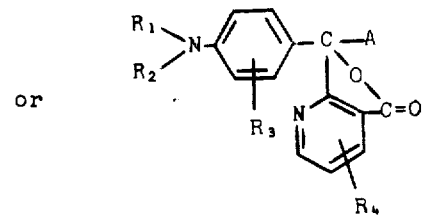

or a mixture thereof, wherein $R_1$, $R_2$, $R_3$, $R_4$ and A are as defined hereinafter, is disclosed.

2 Claims, No Drawings

PRESSURE-SENSITIVE COPYING PAPER CONTAINING LACTONE COMPOUNDS OF PYRIDINE-CARBOXYLIC ACID

BACKGROUND OF THE INVENTION

1. Field of the Invention

This invention relates to a pressure-sensitive copying paper using as a color former a pyridine-carboxylic acid lactone represented by the formula

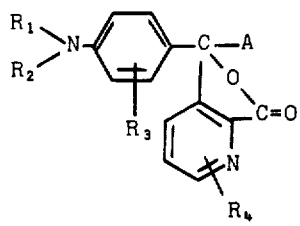

or

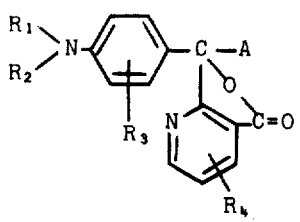

(I)

or a mixture thereof, wherein $R_1$ and $R_2$ each represents a hydrogen atom, an acyl group, a lower alkyl group which may be substituted with a halogen atom, a cyano, hydroxyl, lower alkoxy, lower alkylamino, acetyl or phenoxy group, or a benzyl or phenyl group which may be substituted with a lower alkyl group, a halogen atom, a lower alkoxy, nitro, amino or lower alkylamino group, or $R_1$ and $R_2$ may, when taken with a nitrogen atom to which $R_1$ and $R_2$ are attached, form a part of a saturated hydrocarbon chain of a heterocylic ring; $R_3$ represents a hydrogen or halogen atom, a nitro, amino, lower alkylamino group or a lower alkyl group which may be substituted with a halogen atom or a lower alkoxy group, a lower alkoxy group which may be substituted with a halogen atom, or a benzyl, benzyloxy or phenoxy group which may be substituted with a halogen atom, a lower alkyl, alkoxy or lower alkylamino group; $R_4$ represents a hydrogen or halogen atom, a lower alkyl group or a phenyl group; and A represents a carbazolyl, acridinyl, phenothiazinyl, thienyl, thianaphthenyl, morpholinophenyl, julolidinyl or tetrahydroquinolyl group which may be substituted with a lower alkyl, lower alkylamino, acyl or nitro group; the alkyl moiety in said lower alkyl, lower alkoxy or lower alkylamino group containing 1 to 5 carbon atoms.

2. Description of the Prior Art

In general, pressure-sensitive copying paper comprises the combination of an upper sheet paper (or transfer sheet) having coated on the back surface thereof minute microcapsules containing dissolved therein an electron donative substantially colorless organic compound capable of undergoing color reaction, i.e., color former, and a lower sheet paper (or receiving sheet) having coated on the surface thereof a color developer. When these two coated surfaces are brought into contact with each other and a localized pressure is applied to the assembly by handwriting or typewriting, microcapsules located at the pressure-applied area rupture and the organic color former contained in the organic solvent comes into contact with the color developer to form color.

Color developers which can be used in this invention include active clay substances such as acid clay, attapulgite, zeolite, bentonite; solid organic acids such as succinic acid, tannic acid, benzoic acid; and acidic polymers such as phenolformalin polymers, phenolacetylene polymers, styrene-maleic anhydride polymers containing residual acid groups, salicylic acid-formalin polymers and the like.

As the organic solvent for dissolving the color former, there are ethylene glycol, chlorobenzenes, diethyl phthalate, trioctyl phosphate, dibenzyl benzene, dibenzyl toluene, alkylnaphthalenes and naphthylalkyl alcohols and the like.

SUMMARY OF THE INVENTION

As a result of detailed investigations on the color former for pressure-sensitive copying papers, the present inventors have discovered that there can be obtained a pressure-sensitive copying paper capable of forming a wide variety of colors such as a red, reddish purple, purple, purplish blue, blue, greenish blue, bluish green, green or a like color by using as a color former a novel pyridine-carboxylic acid lactone represented by the above formula (I), and that there can be obtained a pressure-sensitive copying paper capable of forming optional desired color by using the novel color former in combination with a known color former or formers.

DETAILED DESCRIPTION OF THE INVENTION

Pressure-sensitive copying papers using the novel pyridine-carboxylic acid lactone represented by the formula (I) is colorless or slightly colored before color reaction, but, when in contact with the color developer, it immediately forms a red, reddish purple, purple, purplish blue, blue, greenish blue, bluish green, green or a like color with high color density. The thus formed color is excellent in light resistance.

Further, pressure-sensitive copying papers using the novel color former in combination with a known color former or formers immediately form an optional color when brought into contact with the color developer. The thus formed color undergoes little change in hue with the lapse of time after color formation. The lactone color formers of pyridine-carboxylic acid used for pressure-sensitive copying papers of the present invention and the starting material, pyridine-carboxylic acids can be prepared as follows.

1. Preparation of Pyridine-Carboxylic Acid

About 1 mole of a quinolinic anhydride represented by the formula

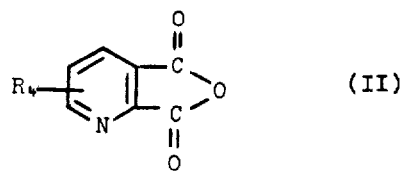

(II)

wherein R₄ is as defined in the formula (I) is reacted with about 1 to 2 moles of an aniline represented by the formula

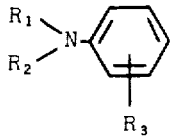

(III)

wherein R₁, R₂ and R₃ are as defined in the formula (I) or a heterocyclic compound represented by the formula

A-H         (IV)

wherein A is as defined in the formula (I) in a volatile organic inert solvent such as carbon disulfide, tetrachloroethane, a chlorobenzene, a nitrobenzene and the like using about 1 to 3 moles of a Friedel-Crafts catalyst such as zinc chloride, phosphorus chloride, aluminum chloride and the like at a temperature of from about 10° to 110°C for a period of about 1 to 9 hours. The reaction mixture is cooled to room temperature and the inert organic solvent is removed by decantation. The resulting reaction product is poured into ice-water or cold dilute aqueous hydrochloric acid to hydrolyze the catalyst. The precipitated solid is filtered, washed successively with water and benzene and dried. Alternatively, after cooling the reaction mixture as above, the reaction mixture is poured into about 2 to 6 l of ice-water to hydrolyze the catalyst. The same inert organic solvent as used above is then added to the resulting aqueous solution to transfer the reaction product to the solvent layer. The solvent layer is recovered by separation and the solvent is distilled off. There is obtained a mixture of isomers of a benzoyl-pyridine-carboxylic acid each represented by the formulae

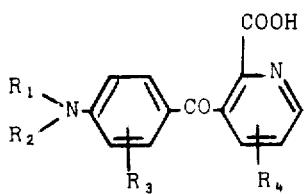

and         (V)

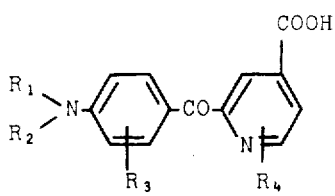

wherein R₁, R₂, R₃ and R₄ are as defined in the formula (I), respectively, or a mixture of isomers of a (heterocyclic-carbonyl)-pyridine-carboxylic acid each represented by the formulae

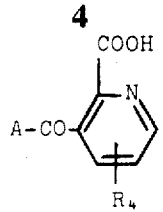

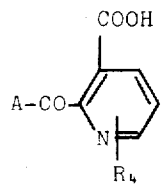

(VI)

wherein A and R₄ are as defined in the formula (I), respectively, as crystals. If necessary, the above obtained isomer mixture can be separated into each isomer in high purity, by 1) dissolving the isomer mixture as above obtained in dilute aqueous sodium hydroxide, carefully adding dilute aqueous hydrochloric acid to the resulting solution in small portions and then recovering each of solids which precipitates due to the difference in pH of the solution or 2) repeatedly recrystallizing the reaction product using a mixture of a less polar solvent such as benzene, toluene and the like and a polar solvent such as methanol, butanol and the like, or a combination of (1) and (2) above. Further, pyridine-carboxylic acid in which two isomers are present in various proportions can also be obtained.

2. Preparation of Lactone Color Former of Pyridine-Carboxylic Acid Represented by the Formula (I)

About 1 mole of the above obtained 3-benzoyl-pyridine-carboxylic acid-(2), 2-benzoyl-pyridine-carboxylic acid-(3) or a mixture thereof is reacted with about 0.9 to 1.5 moles of a heterocyclic compound represented by the formula (IV), or about 1 mole of the above obtained 3-(heterocyclic-carbonyl)-pyridine-carboxylic acid-(2), 2-(heterocyclic-carbonyl)-pyridine-carboxylic acid-(3) or a mixture thereof is reacted with about 0.9 to 1.5 moles of an aniline compound represented by the formula (III), in concentrated sulfuric acid, acetic anhydride or polyphosphoric acid at a temperature of from about 30 to 130°C for about 2 to 10 hours. The reaction mixture is cooled to room temperature and the reaction product is poured into ice-water. The resulting solution is then made weakly acidic or neutral with dilute aqueous sodium hydroxide. Benzene or toluene is added to the solution followed by stirring to transfer any unreacted heterocyclic compound or aniline compound to the benzene or toluene layer which is then removed by separation. The residual aqueous layer is adjusted to a pH of 11 to 12 with dilute aqueous sodium hydroxide. The precipitated solid is collected by filtration, washed successively with water and a small amount of ethanol and dried to give a substantially colorless or slightly colored lactone color former of pyridine-carboxylic acid represented by the formula (I) in high yield. Alternatively, to the above residual aqueous layer adjusted to a pH of 11 to 12, benzene or toluene is added followed by stirring to transfer a lactone color former of pyridine-carboxylic acid to the benzene or toluene layer, which is then recovered by separation. Benzene or toluene is then distilled off from the benzene or toluene layer. The residue is washed successively with water and a small amount of ethanol, benzene, petroleum ether or ligroin and dried to give a substantially colorless or slightly colored lactone color former of pyridine-carboxylic acid represented by the formula (I) in high yield. Or else, the reaction product obtained in the above reaction is poured into ice-water, and the resulting aqueous solution is adjusted to a pH of 11 to 12 with dilute aqueous sodium hydroxide. Benzene or toluene is added thereto followed by stirring to transfer the lactone color former of pyridine-carboxylic acid to the benzene or toluene layer. The benzene or toluene layer is recovered by separation and then worked up in the same manner as described above to give a substantially colorless or slightly colored lactone color former of pyridine-carboxylic acid represented by the formula (I) in high yield. If necessary, the resulting lactone color former of pyridine-carboxylic acid may be recrystallized.

Now, the process for preparing the color former of the present invention, i.e., lactone color formers of pyridine-carboxylic acid will be illustrated by the following Preparation Examples.

PREPARATION EXAMPLE 1 (Color Former Nos. 1 to 3)

10 g of quinolinic anhydride and 26 g of N,N-diethyl-m-phenetidine were added to 100 m of benzene, and 27 g of anhydrous aluminum chloride was added to the mixture in small portions over about 20 minutes while stirring and maintaining the temperature at 30° to 35°C. Upon completion of the addition, the mixture was allowed to react for 4 hours at a temperature in the range of from 35° to 38°C and thereafter was cooled to room temperature. The benzene was removed by decantation, and the resulting reaction product was added to 800 g of ice-water followed by stirring. The precipitated solid was filtered, washed with water and dried to give 15.5 g of an isomer mixture comprising 3-(4'-diethylamino-2'-ethoxybenzoyl)-pyridine-carboxylic acid-(2) and 2-(4'-diethylamino-2'-ethoxybenzoyl)-pyridine-carboxylic acid-(3) as pale brown crystals having a melting point of 245° to 253°C.

15.5 g of the resulting crystals was then dissolved in dilute aqueous sodium hydroxide. Dilute aqueous hydrochloric acid was added to the resulting solution to adjust the pH to 6 and the precipitated solid was filtered (the filtrate was set aside), washed and dried to give 10 g of an isomer mixture comprising predominantly 3-(4'-diethylamino-2'-ethoxybenzoyl)-pyridine-carboxylic acid-(2) and a small amount of 2-(4'-diethylamino-2'-ethoxybenzoyl)-pyridine-carboxylic acid-(3) as pale brown crystals having a melting point of 293° to 297°C. 10 g of the resulting crystals was then repeatedly recrystallized from a mixed solvent of methanol-benzene (1:1 by volume) to give 6.5 g of a highly purified 3-(4'-diethylamino-2'-ethoxybenzoyl)-pyridine-carboxylic acid-(2) as pale yellow crystals having a melting point of 295° to 296°C.

The filtrate having a pH of 6 obtained from the filtration of the above product was then adjusted to a pH of 2 with dilute aqueous hydrochloric acid, and the precipitated solid was filtered, washed with water and dried to give 4 g of an isomer mixture comprising predominantly 2-(4'-diethylamino-2'-ethoxybenzoyl)-pyridine-carboxylic acid-(3) and a small amount of 3-(4'-diethylamino-2'-ethoxybenzoyl)-pyridine-carboxylic acid-(2) as pale brown crystals having a melting point of 176° to 181°C.

4 g of the isomer mixture thus obtained was then repeatedly recrystallized from a mixed solvent of methanol-toluene (1:1 by volume) to give 2.3 g of a highly purified 2-(4'-diethylamino-2'-ethoxybenzoyl)-pyridine-carboxylic acid-(3) as substantially colorless crystals having a melting point of 179 to 180°C.

2.5 g of the above obtained 3-(4'-diethylamino-2'-ethoxybenzoyl)-pyridine-carboxylic acid-(2) and 1.4 g of 1-methyl-2,3,4-trihydroquinoline were added to 15 g of acetic anhydride, and the reaction mixture was allowed to react at a temperature of 80° to 85°C for 3 hours followed by cooling to room temperature. The reaction product was poured into 150 g of ice-water while stirring to hydrolyze the acetic anhydride. After completion of the hydrolysis, benzene was added to the resulting solution. The aqueous solution was then adjusted to a pH of about 6.5 with dilute aqueous sodium hydroxide to transfer any unreacted 1-methyl-2,3,4-trihydroquinoline to the benzene layer, which was then removed by separation. The residual aqueous solution was adjusted to a pH of 12 with dilute aqueous sodium hydroxide, and the precipitated solid was filtered, washed successively with water and a small amount of ethanol and dried to give 2.3 g of 3-[α-{1'-methyl-2',-3',4'-trihydroquinolin-(6')-yl}-α-{4'-diethylamino-2'-ethoxyphenyl}-α-oxy]-methylpyridine-carboxylic acid-(2) lactone (Color Former No. 1) as slightly pale yellow colored crystals having a melting point of 163°C to 165°C.

2.5 g of the above obtained 2-(4'-diethylamino-2'-ethoxybenzoyl)-pyridine-carboxylic acid-(3) having a melting point of 179° to 180°C and 1.4 g of 1-methyl-2,3,4-trihydroquinoline were added to 15 g of acetic anhydride. The mixture was allowed to react at a temperature of 85°to 90°C for 5 hours and thereafter cooled to room temperature. The reaction product was poured into 200 g of ice-water while stirring to hydrolyze the acetic anhydride. After the hydrolysis, 50 ml of benzene was added thereto and the resulting aqueous solution was adjusted to a pH of 11 to 12 with dilute aqueous sodium hydroxide to transfer a lactone color former of a pyridine-carboxylic acid to the benzene layer. The benzene layer was recovered by separation and benzene was distilled off therefrom. The residue was then washed with a small amount of petroleum ether and dried to give 2.5 g of 2-[α-{1'-methyl-2',3',-4'-trihydroquinoline-(6')-yl}-α-{4'-diethylamino-2'-ethoxyphenyl}-α-oxy]-methylpyridin-carboxylic acid-(3)lactone (Color Former No. 2) as pale yellow colored crystals having a melting point of 126° to 128°C.

Further, 2.5 g of the above obtained isomer mixture of pyridine-carboxylic acid having a melting point of 245° to 253°C and 1.5 g of 1-methyl-2,3,4-trihydroquinoline were added to 20 g of acetic anhydride, and the mixture was allowed to react at a temperature of 85° to 95°C for 4 hours followed by cooling to room temperature. The reaction product was poured into 200 g of ice-water while stirring to hydrolyze the acetic anhydride. After completion of the hydrolysis, the aqueous solution was adjusted to a pH of 11 to 12 with dilute aqueous sodium hydroxide. 50 ml of benzene was added thereto and a lactone color former of a pyridine-carboxylic acid was transferred to the benzene layer, which was then recovered by separation. Benzene was distilled off from the benzene layer, and the residue was washed with a small amount of petroleum ether and dried to give 2.4 g of an isomer mixture comprising 3-[α-{1'-methyl-2',3'3',4'4'-trihydroquinolin-(6')-yl}-α-{4'-diethylamino-2'-ethoxyphenyl}-α-oxy]-methylpyridine-carboxylic acid-(2) lactone and 2-[α-{1'-methyl-2',3',4'-trihydroquinolin -(6')-yl}-α-{4'-diethylamino-2'-ethoxyphenyl}-α-oxy]-methylpyridine-carboxylic acid-(3) lactone as pale brown colored crystals having a melting point of 141° to 147°C.

PREPARATION EXAMPLE 2 (Color Former No. 4)

12.0 g of quinolinic anhydride and 24.4 g of julolidine were added to 120 ml of benzene, and 33 g of anhydrous aluminum chloride was added to the resulting mixture in small portions at a temperature of 10° to 20°C for about 30 minutes while stirring. After completion of addition, the mixture was allowed to cool to room temperature. The benzene layer was removed by decantation, and the resulting reaction product was added to 1,200 g of ice-water followed by stirring. The precipitated solid was recovered by filtration, washed with water and dried to obtain 18.0 g of an isomer mixture comprising 3-[julolidine-carbonyl-(6')]-pyridine-carboxylic acid-(2) and 2-[julolidine-carbonyl-(6')]-pyridine-carboxylic acid-(3) as pale brown colored crystals having a melting point of 260° to 265°C.

3.0 g of the above obtained isomer mixture of a pyridine-carboxylic acid and 2.5 g of N,N-dimethylaniline were added to 20 g of acetic anhydride, and the resulting mixture was allowed to react at a temperature of 90° to 95°C for 5 hours followed by cooling to room temperature. The reaction product was poured into 200 g of ice-water while stirring to hydrolyze the acetic anhydride. After completion of the hydrolysis, the resulting solution was adjusted to a pH of 11 to 12 with dilute aqueous sodium hydroxide. 50 ml of benzene was then added thereto to transfer a lactone color former of a pyridine-carboxylic acid to the benzene layer, which was then recovered by separation. Benzene was distilled off from the benzene layer, and the residue was washed with a small amount of petroleum ether and dried to give 2.5 g of an isomer mixture comprising 3-[α-{julolidin -(6')-yl}-α-{4'-dimethylaminophenyl}-α-oxy]-methylpyridine-carboxylic acid-(2) lactone and 2-[α -{julolidin -(6')-yl}-α{4'-dimethylaminophenyl}-α-oxy]-methylpyridine-carboxylic acid-(3) lactone as pale yellow colored crystals having a melting point of 121° to 126°C.

PREPARATION EXAMPLE 3 (Color Former Nos. 5 to 45)

Each of the quinolinic anhydrides (II) and each of the anilins (III) or each of the heterocyclic compounds (IV) which correspond to the color formers were reacted and worked up in the same manner as described in Preparation Example 1 to prepare an isomer mixture of benzoyl-pyridine-carboxylic acids (V) or an isomer mixture of (heterocyclic-carbonyl)-pyridine-carboxylic acids (VI), respectively.

Subsequently, an isomer mixture of benzoyl-pyridine-carboxylic acids (V) and the corresponding heterocyclic compound (IV), or an isomer mixture of (heterocyclic-carbonyl)-pyridine-carboxylic acids (VI) and the corresponding aniline compound (III) were reacted and the reaction product was worked up in the same manner as described in Preparation Example 1 to obtain an isomer mixture of pyridine-carboxylic acid lactones (I) (Color Former Nos. 5 – 45) as colorless or slightly colored crystals, respectively.

The melting points and crystal appearance of the thus obtained color formers, and pyridine-carboxylic acids, aniline compounds, or heterocyclic compounds with the amount thereof which were used in this example are shown in Table 1 below.

TABLE 1

| Color Former | Pyridine-Carboxylic Acid Represented by the Formula (V) or (VI) and Amount Used | Aniline Compound Represented by the Formula (III) or Heterocyclic Compound Represented by the Formula (IV) and Amount Used | Lactone Color Former Represented by the Formula (I) | | |
|---|---|---|---|---|---|
| | | | Yield (g) | Melting Point (°C) | Crystal Appearance |
| No.1 | 3-(4'-Diethylamino-2'-ethoxybenzoyl)-pyridine-carboxylic acid-(2) 2.5 g | 1-Methyl-2,3,4-trihydroquinoline 1.4 g | 3-[α-{1'-Methyl-2',3',4'-trihydroquinolin-(6')-yl}-α-{4'-diethylamino-2'-ethoxyphenyl}-α-oxy]-methylpyridine-carboxylic acid-(2) lactone 2.3 | 163–165 | pale yellow |
| No.2 | 2-(4'-Diethylamino-2'-ethoxybenzoyl)-pyridine-carboxylic acid-(3) 2.5 g | " 1.4 g | 2-[α-{1'-Methyl-2',3',4'-trihydroquinolin-(6')-yl}-α-{4'-diethylamino-2'-ethoxyphenyl}-α-oxy]-methylpyridine-carboxylic acid-(3) lactone 2.5 | 126–128 | pale yellow |
| No.3 | 3-(and 2-)(4'-Diethylamino-2'-ethoxybenzoyl)-pyridine-carboxylic acid-(2)[and-(3)] 3.0 g | " 2.2 g | 3-(and 2-)[α-{1'-Methyl-2',3',4'-trihydroquinolin-(6')-yl}-α-{4'-diethylamino-2'-ethoxyphenyl}-α-oxy]-methylpyridine-carboxylic acid-(2)[and-(3)] lactone 2.4 | 141–147 | pale yellow |
| No.4 | 3-(and 2-)[Julolidine-carbonyl-(6')]-pyridine-carboxylic acid-(2)[and-(3)] 3.0 g | N,N-Dimethylaniline 2.5 g | 3-(and 2-)[α-{Julolidin-(6')-yl}-α-{4'-dimethylaminophenyl}-α-oxy]-methylpyridine-carboxylic acid-(2)[and-(3)] lactone 2.5 | 121–126 | pale yellow |
| No.5 | 3-(and 2-)[α-{1'-Methyl-2',3',4'-trihydroquinoline carbonyl-(6')}]-pyridine-carboxylic acid-(2)[and-(3)] 3.0 g | N-Ethyl-N-β-chloroethyl-aniline 2.5 g | 3-(and 2-)[α-{1'-Methyl-2',3',4'-trihydroquinolin-(6')-yl}-α-{4'-(N-β-chloroethyl-N-ethyl)-aminophenyl}-α-oxy]-methylpyridine-carboxylic acid-(2)[and-(3)] lactone 2.5 | 93–98 | pale yellow |
| No.6 | " 3.0 g | N-Ethyl-N-benzylaniline 2.7 g | 3-(and 2-)[α-{1'-Methyl-2',3',4'-trihydroquinolin-(6')-yl}-α-{4'-(N-benzyl-N-methyl)-aminophenyl}-α-oxy]-methylpyridine-carboxylic acid-(2)[and-(3)] lactone 3.1 | 92–97 | pale yellow |

TABLE 1-continued

| Color Former | Pyridine-Carboxylic Acid Represented by the Formula (V) or (VI) and Amount Used | Aniline Compound Represented by the Formula (III) or Heterocyclic Compound Represented by the Formula (IV) and Amount Used | Lactone Color Former Represented by the Formula (I) | | |
|---|---|---|---|---|---|
| | | | Yield (g) | Melting Point (°C) | Crystal Appearance |
| No.7 | 3-(and 2-)(4'-Dibenzylaminobenzoyl)-pyridine-carboxylic acid-(2)[and-(3)] 4.0 g | 1-Methyl-2,3,4-trihydroquinoline 2.5 g | 3-(and 2-)[α-{1'-Methyl-2',3',4'-trihydroquinolin-(6')-yl}-α-{4'-dibenzylaminophenyl}-α-oxy]-methylpyridine-carboxylic acid-(2)[and-(3)] lactone 4.9 | 129–137 | pale yellow |
| No.8 | 3-(and 2-)(4'-Morpholinobenzoyl)-pyridine-carboxylic acid-(2)[and-(3)] 3.0 g | '' 2.1 g | 3-(and 2-)[α-{4'-Morpholino-phenyl}-α-{1'-methyl-2',3',4'-trihydroquinolin-(6')-yl}-α-oxy]-methylpyridine-carboxylic acid-(2)[and-(3)] lactone 3.1 | 89–96 | pale yellow |
| No.9 | 3-(and 2-)(4'-Diethylamino-2'-methylbenzoyl)-pyridine-carboxylic acid-(2)[and-(3)] 4.0 g | '' 2.7 g | 3-(and 2-)[α-{4'-Diethylamino-2'-methylphenyl}-α-{1'-methyl-2',3',4'-trihydroquinolin-(6')-yl}-α-oxy]-methylpyridine-carboxylic acid-(2)[and-(3)] lactone 4.9 | 132–136 | pale yellow |
| No.10 | 3-(and 2-)[9'-Ethylcarbazolcarbonyl-(3')]-pyridine-carboxylic acid-(2)[and-(3)] 3.7 g | N,N-Dimethylaniline 2.1 g | 3-(and-2)[α-{9'-Ethylcarbazol-(3')-yl}-α-{4'-dimethylaminophenyl}-α-oxy]-methylpyridine-carboxylic acid-(2)[and-(3)] lactone 1.4 | 186–195 | pale yellow |
| No.11 | 3-(and 2-)[Acridine-carbonyl-(2')]-pyridine-carboxylic acid-(2)[and-(3)] 3.3 g | N-Benzyl-N-methylaniline 2.3 g | 3-(and 2-)[α-{Acridin-(2')-yl}-α-{4'-(N-benzyl-N-methyl)-aminophenyl}-α-oxy]-methylpyridine-carboxylic acid-(2)[and-(3)] lactone 1.5 | | pale brown |
| No.12 | 3-(and 2-)[Phenothiazine-carbonyl-(3')]-pyridine-carboxylic acid-(2)[and-(3)] 2.6 g | N-Methyl-N-phenylaniline 1.4 g | 3-(and 2-)[α-{Phenothiazin-(3')-yl}-α-{4'-(N-methyl-N-phenyl)-aminophenyl}-α-oxy]-methylpyridine-carboxylic acid-(2)[and-(3)] lactone 1.3 | | pale yellow |
| No.13 | 3-(and 2-)[10'-Methylphenothiazine-carbonyl-(3')]-pyridine-carboxylic acid-(2)[and-(3)] 3.7 g | N,N-Diethyl-3-chloroaniline 2.4 g | 3-(and 2-)[α-{10'-Methylphenothiazin-(3')-yl}-α-{2'-chloro-4'-diethylaminophenyl}-α-oxy]-methylpyridine-carboxylic acid-(2)[and-(3)] lactone 2.1 | | pale brown |
| No.14 | 3-(and 2-)[Thiophene-carbonyl-(2')]-pyridine-carboxylic acid-(2)[and-(3)] 4.7 g | N-Methyl-N-4''-ethoxyphenyl-aniline 4.1 g | 3-(and 2-)[α-{Thiophen-(2')-yl}-α-{4'-(N-methyl-N-4''-ethoxyphenyl)-aminophenyl}-α-oxy]-methylpyridine-carboxylic acid-(2)[and-(3)] lactone 3.7 | | pale yellow |
| No.15 | 3-(and 2-)Thianaphthene-carbonyl-(2')-pyridine-carboxylic acid-(2)[and-(3)] 2.4 g | N-Acetonylaniline 1.6 g | 3-(and 2-)[α-{Thianaphthen-(2')-yl}-α-{4'-acetonylaminophenyl}-α-oxy]-methylpyridine-carboxylic acid-(2) [and-(3)] lactone 1.3 | | pale yellow |
| No.16 | 3-(and 2-)[4'-(N-Benzyl-N-methyl)-2'-methyl-aminobenzoyl]-pyridine-carboxylic acid-(2)[and-(3)] 4.0 g | 7-Dimethylamino-10-methyl-phenothiazine 4.3 g | 3-(and 2-)[α-{4'-(N-Benzyl-N-ethyl)-amino-2'-methylphenyl}-α-{7'-dimethylamino-10'-methylphenothiazin-(3')-yl}-α-oxy]-methylpyridine-carboxylic acid-(2)[and-(3)] lactone 2.9 | | pale blue |
| No.17 | 3-(and 2-)(4'-Methylaminobenzoyl)-pyridine-carboxylic acid-(2)[and-(3)] 2.0 g | 3-Nitro-9-ethylcarbazole 2.9 g | 3-(and 2-)[α-{4'-Methylaminophenyl}-α-{6'-nitro-9'-ethylcarbazol-(3')-yl}-α-oxy]-methylpyridine-carboxylic acid-(2)[and-(3)] lactone 1.1 | | pale brown |
| No.18 | 3-(and 2-)(4'-Acetamidobenzoyl)-pyridine-carboxylic acid [and-(3)] 2.0 g | 10-Acetylphenothiazine 3.8 g | 3-(and 2-)[α-{4'-Acetamidophenyl}-α-{10'-acetylphenothiazine-(3')-yl}-α-oxy]-methylpyridine-carboxylic acid-(2)[and-(3)] lactone 0.9 | | pale yellow |
| No.19 | Color Former No.19 (0.6g) was hydrolyzed in an ethanol-hydrochloric acid aqueous solution. | | 3-(and 2-) [α-{4'-Aminophenyl}-α-{phenothiazin-(3')-yl}-α-oxy]-methylpyridine-carboxylic acid-(2)[and-(3)} lactone 0.2 | | pale brown |
| No.20 | 3-(and 2-)[4'-(N-4''-Methylphenyl-N-methyl)-aminobenzoyl]pyridine-carboxylic acid-(2)[and-(3)] 3.0 g. | Julolidine 2.1 g | 3-(and 2-)[α-{4'-(N-4''-Methylphenyl-N-methyl)-aminophenyl}-α-{julolidin-(6')-yl}-α-oxy]-methylpyridine-carboxylic acid-(2)[and-(3)] lactone 3.4 | | pale yellow |
| No.21 | 3-(and 2-)[4'-(N-4''-Methylphenyl-N-methyl)-aminobenzoyl]-pyridine-carboxylic acid-(2)[and-(3)] 3.0 g | N,N-Diethyl-3-chloroaniline 2.6 g | 3-(and 2-)[α-{1'-Methyl-2',3',4'-trihydroquinolin-(6')-yl}-α-{4'-(N,N-diethyl)-amino-2'-chlorophenyl}-α-oxy]-methylpyridine-carboxylic acid-(2)[and-(3)]lactone 1.4 | | pale yellow |
| No.22 | ' 3.0 g | N-ethyl-N-β-ethoxyethyl-3-methylaniline 2.9 g | 3-(and 2)-[α-{1'-Methyl-2',3',4'-trihydroquinolin-(6')-yl}-α-{4'-(N-ethyl-N-β-ethoxyethyl)-amino-2-methylphenyl}-α-oxy]-methylpyridine-carboxylic acid-(2)[and-(3)]lactone 3.2 | | pale blue |

TABLE 1-continued

| Color Former | Pyridine-Carboxylic Acid Represented by the Formula (V) or (VI) and Amount Used | Aniline Compound Represented by the Formula (III) or Heterocyclic Compound Represented by the Formula (IV) and Amount Used | Lactone Color Former Represented by the Formula (1) | | |
|---|---|---|---|---|---|
| | | | Yield (g) | Melting Point (°C) | Crystal Appearance |
| No.23 | 3-(and 2-)-{1'-methyl-2', 3',4'-trihydroquinoline-carbonyl-(6')}-pyridine-carboxylic acid - (2)[and -(3) ] 3.0 g | N-β-Diethylaminoethyl-aniline 2.5 g | 3-(and 2-)[α-{1'-Methyl-2',3',4'-tri-hydroquinolin-(6')-yl}-α-{4'-(N-β-diethylaminoethyl)-aminophenyl}-α-oxy]-methylpyridine-carboxylic acid-(2) (and-(3)]lactone 2.4 | | pale yellow |
| No.24 | 3-(and 2-){1'-Methyl-2',3',4'-trihydroquinoline-carboxyl-(6')}-3-chloro-pyridine-carboxylic acid-(2)[and-(3)] 3.0 g | N,N-Dimethyl-3-methoxy-aniline 2.3 g | 3-(and 2-)[α-{1'-Methyl-2',3',4'-tri-hydroquinolin-(6')-yl}-α-{4'-dimethyl-amino-2'-methoxyphenyl}-α-oxy]-methyl-4-chloropyridine-carboxylic acid-(2) [and-(3)]lactone 3.3 | | pale blue |
| No.25 | 3-(and 2-){1'-Methyl-2',3',4'-trihydroquinoline-carbonyl-(6')}-3-methyl-pyridine-carboxylic acid-(2)[and-(3)] | N,N-Diethyl-3-nitroaniline 2.6 g | 3-(and 2-)[α-{1'-Methyl-2',3',4'-tri-hydroquinolin-(6')-yl}-α-{4'-diethyl-amino-2'-nitrophenyl}-α-oxy]-methyl-4-methylpyridine-carboxylic acid-(2) [and-(3)]lactone 0.4 | | pale yellow |
| No.26 | 3-(and 2-){1'-Methyl-2',3',4'-trihydroquinoline-carbonyl-(6')}-2-phenyl-pyridine-carboxylic acid-(2)[and-(3)] 3.0 g | 3.0 g N,N-Dimethylaniline 2.1 g | 3-(and 2-)[α-{1'-Methyl-2',3',4'-tri-hydroquinolin-(6')-yl}-α-{4'-dimethyl-aminophenyl}-α-oxy]-methyl-6-phenyl-pyridine-carboxylic acid-(2)[and-(3)] lactone 0.9 | | pale brown |
| No.27 | 3-(and 2-){1'-Methyl-2',3',4'-trihydroquinoline-carbonyl-(6')}-pyridine-carboxylic acid-(2)[and-(3)] 3.0 g | N-Methyl-N-4'-methylphenyl-aniline 2.7 g | 3-(and 2-)[α-{1'-Methyl-2',3',4'-tri-hydroquinolin-(6')-yl}-α-{4'-(N-methyl-N-4''-methylphenyl)-aminophenyl}-α-oxy]-methylpyridine-carboxylic acid-(2)[and-(3)]lactone 2.1 | | pale blue |
| No.28 | '' 3.0 g | N-β-Oxylethyl-N-β-cyano-ethylaniline 2.6 g | 3-(and 2-)[α-{1'-Methyl-2',3',4'-tri-hydroquinolin-(6')-yl}-α-{4'-(N-β-hydroxyethyl-N-β-cyanoethyl)-amino-phenyl}-α-oxy]-methylpyridine-carboxylic acid-(2)[and-(3)]lactone 1.3 | | pale blue |
| No.29 | '' 3.0 g | N-Benzoylaniline 2.4 g | 3-(and 2-)[α-{1'-Methyl-2',3',4'-tri-hydroquinolin-(6')-yl}-α-{4'-benzamido-phenyl}-α-oxy]-methylpyridine-carboxylic acid-(2)[and-(3)]lactone 0.4 | | pale brown |
| No.30 | 3-(and-2){Julolidine-carbonyl-(6')}-pyridine-carboxylic acid-(2)[and-(3)] 3.0 g | N-Methyl-N-4'-chlorophenyl-aniline 2.4 g | 3-(and 2-)[α-{Julolidin-(6')-yl}-α-{4'-(N-4''-chlorophenyl-N-methyl)-amino-phenyl}-α-oxy]-methylpyridine-carboxylic acid-(2)[and-(3)]lactone 1.3 | | pale yellow |
| No.31 | '' 3.0 g | 4,4'-bis-Dimethylamino-phenylmethane 3.4 g | 3-(and 2-)[α-{Julolidin-(6')-yl}-α-{4'-dimethylamino-2'-(4''-dimethylamino)-benzylphenyl}-α-oxy]-methylpyridine-carboxylic acid-(2)[and-(3)] lactone 1.9 | | pale green |
| No.32 | '' 3.0 g | N-Ethyl-N-4'-Nitrobenzyl-aniline 3.1 g | 3-(and 2-)[α-{Julolidin-(6')-yl}-α-{4'-(N-ethyl-N-4''-nitrobenzyl)-aminophenyl}-α-oxy]-methylpyridine-carboxylic acid-(2)[and-(3)]lactone 1.3 | | pale brown |
| No.33 | '' 3.0 g | N,N-Dimethyl-3-(4'-chloro)-phenoxyaniline 2.5 g | 3-(and 2-)[α-{Julolidin-(6')-yl}-α-{4'-dimethylamino-2'-(4''-chlorophenoxy)-phenyl}-α-oxy]-methylpyridine-carboxylic acid-(2)[and-(3)]lactone 2.1 | | pale green |
| No.34 | 3-(and-2){Julolidine-carbonyl-(6')}-pyridine-carboxylic acid-(2)[and-(3)] 3.0 g | N,N-Dimethyl-3-(4'-methyl)-benzyloxyaniline 2.9 g | 3-(and 2-)[α-{Julolidin-(6')-yl}-α-{4'-dimethylamino-3'-(4''-methyl)-benzyloxyphenyl}-α-oxy]-methylpyridine-carboxylic acid-(2)[and-(3)]lactone 2.3 | | pale green |
| No.35 | 3-(and 2-){4'-(Pyrrolidin-(1'')-yl)-benzoyl}-pyridine-carboxylic acid-(2)[and-(3)] 2.5 g | Thionaphtene 1.7 g | 3-(and 2-)[α-{4'-(Pyrrolidin-(1'')-yl) phenyl}-α-{thionaphten-(2')-yl}-α-oxyl]-methylpyridine-carboxylic acid-(2)[ and-(3)]lactone 2.5 | | pale yellow |
| No.36 | 3-(and 2-){4'-Piperazin-(1'')-yl}-benzoyl}-pyridine-carboxylic acid-(2)[and-(3)] 2.5 g | 1-Methyl-2,3,4-trihydro-quinoline 1.7 g | 3-(and 2-)[α-{1'-Methyl-2',3',4'-tri-hydroquinolin-(6')-yl}-α-{4'-(piperizin-(1'')-yl)-phenyl}-α-oxy]-methylpyridine-carboxylic acid-(2)[and-(3)]lactone 2.8 | | pale yellow |
| No.37 | 3-(and 2-)(4'-Piperidino-benzoyl)-pyridine-carboxylic acid-(2)[and-(3)] 2.5 g | Julolidine 1.9 | 3-(and 2-)[α-{Julolidin-(6')-yl}-α-{4'-piperidinophenyl}-α-oxy]-methylpyridine-carboxylic acid-(2)[and-(3)]lactone 3.1 | | pale yellow |
| No.38 | 3-(and 2-)(4'-Diethylamino-2'-methylaminobenzoyl)-pyridine-carboxylic acid-(2)[and-(3)] 2.0 g | Thionaphthene 0.8 g | 3-(and 2-)[α-{4'-Diethylamino-2'-methyl-aminophenyl}-α-{thionaphthen-2'-yl}-α-oxy-methylpyridine-carboxylic acid-(2)[and-(3)]lactone 1.9 | | pale brown |

TABLE 1-continued

| Color Former | Pyridine-Carboxylic Acid Represented by the Formula (V) or (VI) and Amount Used | Aniline Compound Represented by the Formula (III) or Heterocyclic Compound Represented by the Formula (IV) and Amount Used | Lactone Color Former Represented by the Formula (I) | | |
|---|---|---|---|---|---|
| | | | Yield (g) | Melting Point (°C) | Crystal Appearance |
| No.39 | 3-(and 2-){4'-(N-Phenoxyethyl-N-ethyl)-amino-2'-methylbenzoyl}-pyridine-carboxylic acid-(2)[and-(3)] 3.0 g | Thiophene 0.9 g | 3-(and 2-)[α-{4'-(N-Phenoxyethyl-N-ethyl)-amino-2'-methylphenyl}-α-{thiophen-(2')-yl}-α-oxy]-methylpyridine-carboxylic acid-(2)[and-(3)]lactone | | |
| No.40 | 3-(and 2-){4'-Dimethylamino-2'-(4''-dimethylamino)-benzylbenzoyl}-pyridine-carboxylic acid-(2)[and-(3)] 3.0 g | Julolidine 1.8 g | 3-(and 2-)[α-{Julolidin-(6')-yl}-α-{4'-dimethylamino-2'-(4''-dimethylamino)-benzylphenyl}-α-oxy]-methylpyridine-carboxylic acid-(2)[and-(3)]lactone | 2.7 | pale yellow |
| No.41 | 3-(and 2-){4'-Diethylamino-2'-(4''-methyl)-benzylbenzoyl}-pyridine-carboxylic acid-(2)[and-(3)] 3.0 g | 1-Methyl-2,3,4-trihydroquinoline 1.6 g | 3-(and 2-)[α-{1'-Methyl-2',3',4'-trihydroquinolin-(6')-yl}-α-{4'-diethylamino-2'-(4''-methyl)-benzylphenyl}-α-oxy]-methylpyridine-carboxylic acid-(2)[and-(3)]lactone | 3.7 | pale blue |
| No.42 | 3-(and 2-)(4'-Diethylamino-2'-methoxymethylbenzoyl)-pyridine-carboxylic acid-(2)[and-(3)] 2.5 g | 9-Ethylcarbazole 1.9 g | 3-(and 2-)[α-{9'-Ethylcarbazol-(3')-yl}-α-{4'-diethylamino-2'-methoxymethylphenyl}-α-oxy]-methylpyridine-carboxylic acid-(2)[and-(3)]lactone | 3.2 | pale yellow |
| No.43 | 3-(and 2-){4'-(N-Dimethylamonophenyl-N-methyl)-benzoyl}-pyridine-carboxylic acid-(2)[and-(3)] 3.0 g | Julolidine 1.9 | 3-(and 2-)[α-{Julolidin-(6')-yl}-α-{4'-(N-4''-dimethylaminophenyl-N-methyl)-amonophenyl}-α-oxy]-methylpyridine-carboxylic acid-(2)[and-(3)]lactone | 2.1 | pale yellow |
| No.44 | 3-(and-2){4'-(N-4''-Dimethylaminobenzyl-N-methyl)-aminobenzoyl}-pyridine-carboxylic acid-(2)[and-(3)] 3.0 g | 1-Methyl-2,3,4-trihydroquinoline 1.4 g | 3-(and 2-)[α-{1'-Methyl-2',3',4'-trihydroquinolin-(6')-yl}-α-{4'-(N-4''-dimethylaminobenzyl-N-methyl)-aminophenyl}-α-oxy]-methylpyridine-carboxylic acid-(2)[and-(3)]lactone | 3.5 | pale green |
| No.45 | 3-(and 2-)(4'-Morpholino-benzoyl)-pyridine-carboxylic acid-(2)[and-(3)] 2.5 g | N-Phenylmorpholine 1.5 g | 3-(and 2-)[α,α-bis(4'-Morpholinophenyl)-oxy]-methylpyridine-carboxylic acid-(2)[and-(3)]lactone | 3.1 | pale yellow |
| | | | 3.1 | | pale yellow |

The processes for producing pressure-sensitive copying papers using pyridine-carboxylic acid lactones represented by the formula (I) as a color former are well known in the art and include the method in which phenomenon of complex coacervation is utilized to produce microcapsules as disclosed in U.S. Pat. Nos. 2,800,457 and 2,800,458. The color former is generally used in an amount of from about 0.5 to 5% by weight based on the previously described organic solvent such as ethylene glycol, chlorobenzenes, diphenyl chloride, dibenzylbenzene, dibenzyltoluene, diethylphthalate, trioctyl phosphate, an alkylnaphthalene and naphthylalkyl alcohols, etc.

The pressure-sensitive copying paper using pyridine-carboxylic acid lactones represented by the formula (I) will now be illustrated in greater detail by the following Example, but they are not to be construed as limiting the scope of this invention. In these examples, all percentages, parts and the like are by weight unless otherwise indicated.

EXAMPLE 1

2.0 g of Color Former Nos. 1 to 3 were taken up and treated as follows. Each color former was dissolved in 100 g of dibenzyl toluene, and 20 g of gum arabic and 160 g of water were added thereto at a temperature of 50°C to emulsify. To the resulting emulsion were added 20 g of acid-treated gelatin and 160 g of water and, under stirring, acetic acid was added thereto to adjust the pH to 5. 500 g of water was then added thereto to allow coacervation to proceed thereby forming thick, liquid film of gelatin-gum arabic around oil droplets of dibenzyl toluene having the color former dissolved therein. After adjusting the pH to 4.4, 4 g of a 37% formalin aqueous solution was added thereto to harden the above-described liquid film. Then, the system was cooled to 10°C and, after adjusting the pH to 9 with dilute aqueous sodium hydroxide, allowed to stand for 5 to 6 hours to complete encapsulation.

The resulting microcapsule-containing liquid was applied to paper by a coating method such as roll-coating and air knife-coating, etc., and dried to obtain a colorless coated paper (upper sheet paper). When this upper sheet paper was intimately superposed on a lower sheet paper having coated thereon an active clay substance as a color developer and a localized pressure was applied to the assembly by handwriting, a greenish blue color was immediately formed on the lower sheet paper at the pressed area. There was observed almost no discoloration nor fading of the thus developed greenish blue color even when it was exposed directly to sunlight for a long period of time.

Alternatively, when the upper sheet paper was intimately superposed on a lower sheet paper having coated thereon an acidic organic polymer and a localized pressure was applied thereto by handwriting, a greenish blue color was immediately formed on the lower sheet paper at the pressure-applied area.

EXAMPLE 2

2.0 g of Color Former No. 4 was taken up and treated in the same manner as described in Example 1. After coating and drying, there was obtained a colorless upper sheet paper. When this upper sheet paper was intimately superposed on a lower sheet paper having coated thereon an active clay substance as a color developer and a localized pressure was applied thereto by handwriting, there was immediately developed a blue color on the lower sheet paper at the pressed area. There was observed almost no discoloration nor fading of the thus developed blue color even when it was directly exposed to sunlight for a long period of time. Alternatively, when the upper sheet paper was intimately superposed on a lower sheet paper having coated thereto an acidic organic polymer as the color developer and a localized pressure was applied to the assembly by handwriting, a blue color was immediately developed on the lower sheet paper at the pressed area.

EXAMPLE 3

2.0 g of each of Color Former Nos. 5 to 8 was taken up and treated in the same manner as described in Example 1. After coating and drying, there was obtained a colorless upper sheet paper. The resulting paper was intimately superposed on a lower sheet paper having coated thereon an acidic organic polymer, an acid clay substances or a combination thereof, as a color developer. When a localized pressure was applied to the assembly, a blue color was immediately formed on the lower sheet paper at the pressed area. The thus formed blue color exhibited a sufficient stability to the lapse of time for practical use.

EXAMPLE 4

2.0 g of each of Color Former Nos. 9 to 45 were taken up and each of them was treated in the same manner as described in Example 1. After coating and drying, there were obtained colorless upper sheet papers. When each of the resulting papers was intimately superposed on a lower sheet paper having coated thereon an acid clay substance as a color developer, and a localized pressure was applied to the assembly by handwriting, there was immediately developed a deep color image on the lower sheet paper at the pressed area. The thus developed color images showed sufficient stability to the lapse of time for practical use.

The hues developed on the lower sheets are shown in Table 2 below.

TABLE 2

| Color Former | Hue | Color Former | Hue |
| --- | --- | --- | --- |
| No. 9 | bluish green | No. 28 | blue |
| No. 10 | purplish blue | No. 29 | purple |
| No. 11 | " | No. 30 | blue |
| No. 12 | " | No. 31 | bluish green |
| No. 13 | " | No. 32 | purplish blue |
| No. 14 | purple | No. 33 | green |
| No. 15 | reddish purple | No. 34 | " |
| No. 16 | blue | No. 35 | purple |
| No. 17 | reddish purple | No. 36 | bluish purple |
| No. 18 | red | No. 37 | blue |
| No. 19 | " | No. 38 | greenish blue |
| No. 20 | blue | No. 39 | blue |
| No. 21 | " | No. 40 | " |
| No. 22 | greenish blue | No. 41 | " |
| No. 23 | blue | No. 42 | " |
| No. 24 | bluish green | No. 43 | green |
| No. 25 | purple | No. 44 | greenish blue |
| No. 26 | blue | No. 45 | blue |
| No. 27 | bluish green | | |

EXAMPLE 5

2.1 g of Color Former No. 3, 2.4 of Color Former No. 21, 0.3 g of o-hydroxybenzalacetophenone, 0.1 g of Rhodamine B-anilinolactam, and 0.3 g of benzoyl leucomethylene blue were treated and coated in the same manner as described in Example 1 to prepare an upper sheet paper. When this upper sheet paper was superposed on a lower sheet having coated thereon an active clay substance as a color developer and a localized pressure was applied to the assembly by handwriting, a black color was immediately developed on the lower sheet paper. The thus developed black color scarcely underwent change in hue and fading.

While the invention has been described in detail and with reference to specific embodiments thereof, it will be apparent to one skilled in the art that various changes and modifications can be made therein without departing from the spirit and scope thereof.

What is claimed is:

1. A pressure-sensitive copying paper coated with a microencapsulated using as a color former a lactone compound of a pyridine-carboxylic acid represented by the formula

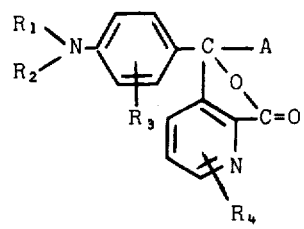

or

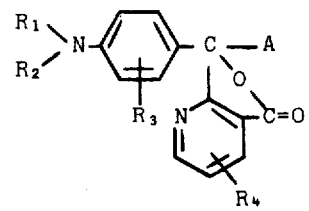

(I)

or a mixture thereof, wherein $R_1$ and $R_2$ each represents a hydrogen atom, an acyl group, a lower alkyl group which may be substituted with a halogen atom, a cyano, hydroxyl, lower alkoxy, lower alkylamino, acetyl or phenoxy group, or a benzyl or phenyl group which may be substituted with a lower alkyl group, a halogen atom, a lower alkoxy, nitro, amino or lower alkylamino group, or $R_1$ and $R_2$ may, when taken together with a nitrogen atom to which $R_1$ and $R_2$ are attached, form a part of a saturated hydrocarbon chain of a heterocyclic ring; $R_3$ represents a hydrogen or halogen atom, a nitro, amino, lower alkylamino group or a lower alkyl group which may be substituted with a halogen atom or a lower alkoxy group, a lower alkoxy group which may be substituted with a halogen atom, or a benzyl, benzyloxy or phenoxy group which may be substituted with a halogen atom, a lower alkyl, alkoxy or lower alkylamino group; $R_4$ represents a hydrogen or halogen atom, a lower alkyl group or a phenyl group; and A represents a carbazolyl, acridinyl, phenothiazinyl, thienyl, thianaphthenyl, morpholinophenyl, julolidinyl or tetrahydroquinolyl group which may be substituted with a lower alkyl, lower alkylamino, acyl or nitro group; the alkyl moiety in said lower alkyl, lower alkoxy or lower alkylamino group containing 1 to 5 carbon atoms.

2. The pressure-sensitive copying paper as claimed in claim 1, wherein said color former is a compound selected from the group consisting of a. 3-[α-{1'-methyl-2', 3', 4'-trihydroquinolin-(6')-yl}-α-{4'-diethylamino-2'-ethoxyphenyl}-α-oxy]-methylpyridine-carboxylic acid-(2)lactone,
b. 2-[α-{1'-methyl-2', 3', 4'-trihydroquinolin-(6')-yl}-α-{4'-diethylamino-2'-ethoxyphenyl}-α-oxy]-methylpyridine-carboxylic acid-(3) lactone,
c. an isomer mixture of (a) and (b) above,
d. an isomer mixture of 3-[α-{julolidin-(6')-yl}-α-{4'-dimethylaminophenyl}-α-oxy]-methypyridine-carboxylic acid-(2) lactone and 2-[α-{julolidin-(6')-yl}-α-{4'-dimethylaminophenyl}-α-oxy]-methypyridine-carboxylic acid-(3) lactone,
e. an isomer mixture of 3-[α-{1'-methyl-2', 3', 4'-trihydroquinolin-(6')-yl}-α-{4'-(N-β-chloroethyl-N-ethyl)-amino-phenyl}-α-oxy]-methylpyridine-carboxylic acid-(2) lactone and 2-[α-{1'-methyl-2', 3', 4'-trihydroquinolin-(6')-yl}-α-{4'-(N-β-chloroethyl-N-ethyl)-aminophenyl}-α-oxy]-methyl-pyridine-carboxylic acid-(3) lactone,
f. an isomer mixture of 3-[α-{1'-methyl-2', 3', 4'-trihydroquinolin-(6')-yl}-α-{4'-dibenzylaminophenyl}-α-oxy]-methylpyridine-carboxylic acid-(2) lactone and 2-[α-{1'-methyl2', 3', 4'-trihydroquinolin-(6')-yl}-α-{4'-dibenzylaminophenyl}α-oxy]-methylpyridine-carboxylic acid-(3) lactone,
g. an isomer mixture of 3-[α-{4-morpholinophenyl}-α-{1'-methyl-2', 3', 4'-trihydroquinolin-(6')-yl}-α-oxy]-methylpyridine-carboxylic acid-(2) lactone and 2-[α-{4'-morpholinophenyl}-α1{1'-methyl-2', 3', 4'-trihydroquinolin-(6')-yl}-α-oxy]-methypyridine-carboxylic acid-(3) lactone,
h. an isomer mixture of 3-[α-{9'-ethylcarbazol-(3')-yl}-α-{4'-dimethylaminophenyl}-α-oxy]-methyl-pyridine-carboxylic acid-(2) lactone and 2-[α-{9'-ethylcarbazol-(3')-yl}-α-{4'-dimethylaminophenyl}-α-oxy]-methylpyridine-carboxylic acid-(3) lactone,
i. an isomer mixture of 3-[α-{acridin-(2')-yl}-α-{4'-(N-benzyl-N-methyl)-aminophenyl}-α-oxy]-methylpyridine-carboxylic acid-(2) lactone and 2-[α-{acridin-(2')-yl}-α-{4'-(N-benzyl-N-methyl)-aminophenyl}-α-oxy]-methypyridine-carboxylic acid-(3) lactone,
j. an isomer mixture of 3-[α-{phenothiazin-(3')-yl}-α-{4'-(N-methyl-N-phenyl)-aminophenyl}-α-oxy]-methylpyridine-carboxylic acid-(2) lactone and 2-[α-{phenothiazin-(3')-yl}-α-{4'-(N-methyl-N-phenyl)-aminophenyl}-α-oxy]-methylpyridine-carboxylic acid-(3) lactone,
k. an isomer mixture of 3-[α-{thiophen-(2')-yl}-α-{4'-(N-methyl-N-4''-ethoxyphenyl)-aminophenyl}-α-oxy]-methylpyridine-carboxylic acid-(2) lactone and 2-[α-{thiophen-(2')-yl}-α-{4'-(N-methyl-N-4''-ethoxyphenyl)-aminophenyl}-α-oxy]-methylpyridine-carboxylic acid-(3) lactone,
l. an isomer mixture of 3-[α-{thianaphthen-(2')-yl}-α-{4'-acetonylaminophenyl}-α-oxy]-methylpyridine-carboxylic acid-(2) lactone and 2-[α-{thianaphthen-(2')-yl}-α-{4'-acetonylaminophenyl}-α-oxy]-methylpyridine-carboxylic acid-(3) lactone,
m. an isomer mixture of 3-[α-{4'-methylaminophenyl}-α-{6'-nitro-9'-ethylcarbazol-(3')-yl}-α-oxy]-methylpyridine-carboxylic acid-(2) lactone and 2-[α-{4'-methyl-aminophenyl}-α-{6'-nitro-9'-ethylcarbazol-(3')-yl}-α-oxy]-methylpyridine-carboxylic acid-(3) lactone,
n. an isomer mixture of 3-[α-{1'-methyl-2', 3', 4'-trihydroquinolin-(6')-yl}-α-{4'-diethylamino-2'-nitrophenyl}-α-oxy]-methyl-4-methylpyridine-carboxylic acid-(2) lactone and 2-[α-{1'-methyl-2', 3', 4'-trihydroquinolin-(6')-yl}-α-{4'-diethylamino-2'-nitrophenyl}-α-oxy]-methyl-4-methylpyridine-carboxylic acid-(3) lactone,
o. an isomer mixture of 3-[α-{1'-methyl-2', 3', 4'-trihydroquinolin-(6')-yl}-α-{4'-benzamidophenyl}-α-oxy]-methyl-pyridine-carboxylic acid-(2) lactone and 2-[α-{1'-methyl-2', 3', 4'-trihydroquinolin-(6')-yl}-α-{4'-benzamiodphenyl}-α-oxy]-methylpyridine-carboxylic acid-(3) lactone,
p. an isomer mixture of 3-[α-{julolidin-(6')-yl}-α-{4'-piperidinophenyl}-α-oxy]-methylpyridine-carboxylic acid-(2) lactone and 2-[α-{julolidin-(6')-yl}-α-{4'-piperidinophenyl}-α-oxy]-methylpyridine-carboxylic acid-(3) lactone,
q. an isomer mixture of 3-[α-{1'-methyl-2', 3', 4'-trihydroquinolin-(6')-yl}-α-{4'-diethylamino-2'-(4''-methyl)-benzyl-phenyl}-α-oxy]-methylpyridine-carboxylic acid-(2) lactone and 2-[α-{1'-methyl-2', 3', 4'-trihydroquinolin-(6')-yl}-α-{4'-diethylamino-2'-(4''-methyl)-benzylphenyl}-α-oxy]-methylpyridine-carboxylic acid-(3) lactone,
r. an isomer mixture of 3-[α-{9'-ethylcarbazol-(3')-yl}-α-{4'-diethylamino-2'-methoxymethylphenyl}-α-oxy]-methylpyridine-carboxylic acid-(2) lactone and 2-[α-{9'-ethylcarbazol-(3')-yl}-α-{4'-diethylamino-2'-methoxymethylphenyl}-α-oxy]-methylpyridine-carboxylic acid-(3) lactone, and
s. an isomer mixture of 3-[α, α-bis (4'-morpholinophenyl)-α-oxy]-methylpyridine-carboxylic acid-(2) lactone and 2-[α, α-bis(4'-morpholinophenyl)-α-oxy]-methylpyridine-carboxylic acid-(3) lactone.

* * * * *